United States Patent
Petersen et al.

(10) Patent No.: US 9,743,197 B2
(45) Date of Patent: Aug. 22, 2017

(54) METHOD, DEVICE AND SYSTEM FOR INCREASING A PERSON'S ABILITY TO SUPPRESS NON-WANTED AUDITORY PERCEPTS

(71) Applicant: Oticon A/S, Smørum (DK)

(72) Inventors: Eline Borch Petersen, Smørum (DK); Thomas Lunner, Smørum (DK); Niels Henrik Pontoppidan, Smørum (DK)

(73) Assignee: OTICON A/S, Smørum (DK)

( * ) Notice: Subject to any disclaimer, the term of this patent is extended or adjusted under 35 U.S.C. 154(b) by 0 days.

(21) Appl. No.: 15/061,000

(22) Filed: Mar. 4, 2016

(65) Prior Publication Data
US 2016/0261962 A1    Sep. 8, 2016

(30) Foreign Application Priority Data

Mar. 6, 2015   (EP) .................................. 15158050

(51) Int. Cl.
*H04H 60/33* (2008.01)
*H04R 25/00* (2006.01)
(Continued)

(52) U.S. Cl.
CPC ......... *H04R 25/505* (2013.01); *A61B 5/0402* (2013.01); *A61B 5/0476* (2013.01);
(Continued)

(58) Field of Classification Search
CPC combination set(s) only.
See application file for complete search history.

(56) References Cited

U.S. PATENT DOCUMENTS

| 9,367,131 B2 * | 6/2016 | Klappert ................. G06F 3/015 |
| 2013/0202119 A1 | 8/2013 | Thiede |
| 2014/0169596 A1 | 6/2014 | Lunner et al. |

FOREIGN PATENT DOCUMENTS

| EP | 2200347 A2 | 6/2010 |
| EP | 2200347 A3 | 3/2011 |
| WO | WO 2013/014210 A1 | 1/2013 |

* cited by examiner

*Primary Examiner* — Amir Etesam
(74) *Attorney, Agent, or Firm* — Birch, Stewart, Kolasch & Birch, LLP

(57) ABSTRACT

The present disclosure relates to a method for reducing a listener's task-irrelevant auditory perception, the method comprising providing a measuring device or system configured for measuring the listener's alpha, beta gamma and/or theta activity and providing a generation device or system configured for generating an alpha, beta, gamma and/or theta activity boosting signal that, when provided to the listener will increase the listener's ongoing alpha, beta, gamma and/or theta activity. The listener's alpha, beta, gamma and/or theta activity is measured and if the measured alpha, beta, gamma and/or theta activity is below a predefined threshold, the listener's ongoing alpha, beta, gamma and/or theta activity is increased by the provision of the alpha, beta, gamma and/or theta activity boosting signal to the listener. This results in the listener's ongoing alpha, beta, gamma and/or theta activity being increased, resulting in facilitating reduction of task-irrelevant auditory perception, such as the auditory perception of noise or tinnitus, and thereby also increasing the listener's ability to understand speech under adverse listening conditions. The present disclosure further suggests using the listener's measured alpha, beta, gamma and/or theta activity to judge if the listener is ready to understand speech, and if this is not the case to delay a speech signal until a sufficiently high activity is present.

20 Claims, 5 Drawing Sheets

(51) Int. Cl.
  *A61N 1/36*    (2006.01)
  *A61B 5/0476*  (2006.01)
  *A61B 5/0496*  (2006.01)
  *A61B 5/0402*  (2006.01)
  *A61B 5/053*   (2006.01)
  *A61B 5/12*    (2006.01)
  *A61M 21/00*   (2006.01)
  *A61B 5/16*    (2006.01)
  *H04R 3/00*    (2006.01)

(52) U.S. Cl.
  CPC .......... *A61B 5/0496* (2013.01); *A61B 5/0531* (2013.01); *A61B 5/125* (2013.01); *A61B 5/16* (2013.01); *A61M 21/00* (2013.01); *A61N 1/36032* (2013.01); *H04R 25/75* (2013.01); *H04R 3/00* (2013.01); *H04R 25/50* (2013.01); *H04R 2225/41* (2013.01); *H04R 2225/43* (2013.01)

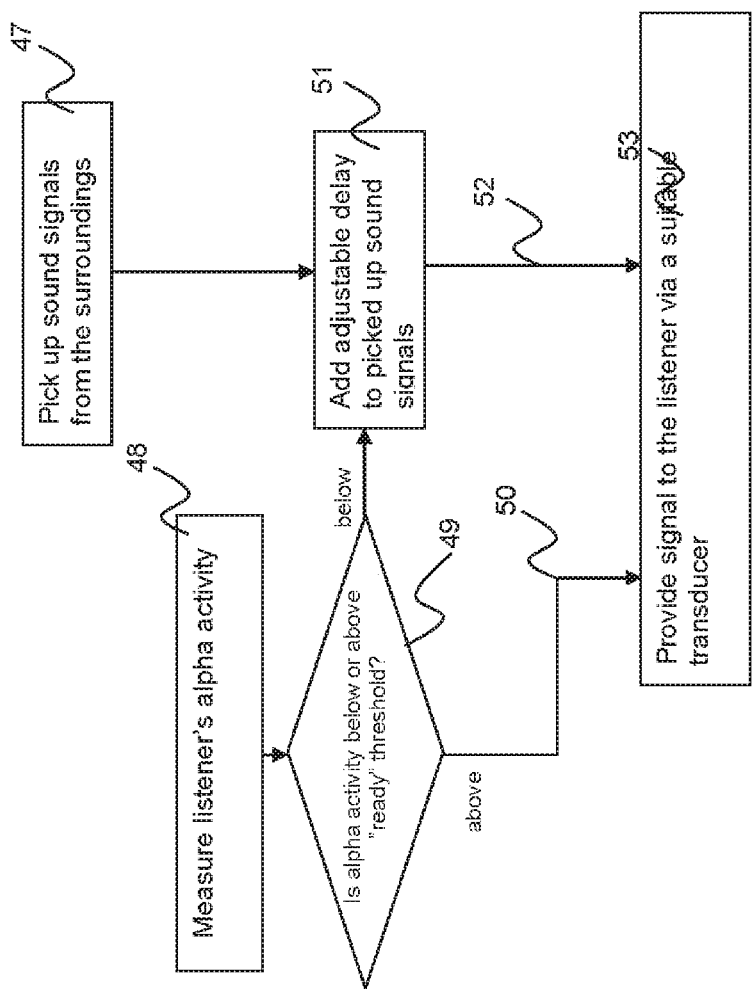

METHOD, DEVICE AND SYSTEM FOR INCREASING A PERSON'S ABILITY TO SUPPRESS NON-WANTED AUDITORY PERCEPTS

FIELD

The present disclosure relates generally to methods, devices and systems for increasing a person's ability to suppress non-wanted auditory percepts, such as background noise, competing speech or tinnitus. More specifically the present disclosure relates to methods, devices and systems for increasing speech perception under adverse listening conditions and still more specifically the present disclosure relates to a hearing instrument, such as a hearing aid incorporating the methods, devices and systems according to the present disclosure.

BACKGROUND OF THE DISCLOSURE

Understanding speech in real world situations, require the involvement of the working memory, which has been linked to alpha activity (approximately 6-13 Hz, such as around 10 Hz). As a consequence of harder listening conditions, an increase in alpha activity is seen. With the alpha activity being linked to inhibition of brain activity, an increase in alpha activity is interpreted as a way of suppressing task-irrelevant information/processes in order to better overcome the listening task at hand. The level of alpha activity (specifically a decrease of alpha power peak frequency) that can be generated differs between individuals, but generally decreases with age. This age-related decline in alpha activity together with individual differences might result in subjects being unable to generate enough alpha activity to successfully suppress irrelevant information and thereby overcome difficult listening situations.

Therefore, there is a need to provide a solution that generally increases a listener's ability to understand speech under adverse listening conditions despite the listener's age-related increased difficulty in processing two different auditory percepts (such as noise and speech) simultaneously.

More specifically, there is a need to provide a hearing instrument, such as a hearing aid, and a corresponding method that offers the above advantages.

Still more specifically, there is a need to provide a hearing instrument, such as a hearing aid, and a corresponding method that can be optimized to a specific user.

SUMMARY OF THE DISCLOSURE

According to the present disclosure the above and further problems that a listener may encounter under adverse listening conditions are solved by estimating a user's (for instance a hearing impaired user's) alpha activity. If this alpha activity is judged to be sufficiently high, i.e. above a specific threshold, an audio signal (that may contain a combination of a speech signal and a noise signal) is presented to the user. If the user's alpha activity is judged to be too low, i.e. below the specific threshold, the present disclosure proposes either to delay the audio signal, until the user's alpha activity becomes sufficiently high and/or to boost the user's alpha activity until it becomes as high as possible.

Specifically, according to preferred implementations of the present disclosure, this boost of alpha activity generation is obtained through neural entrainment. Neuronal entrainment refers to the manipulation of neurons' oscillation phase to promoteneuronal activity. Entrainment has been proven to occur both for amplitude and frequency modulated signals, where an enhancement of the frequency with which the stimuli is modulated is seen in the EEG spectrum.

The neural entrainment can be accomplished through amplitude or frequency entrainment. In a specific embodiment of the present disclosure, the amplitude and/or frequency of the entrainment (i.e. of an entrainment signal provided to the user) can be optimized to the specific user.

According to the present disclosure a user is presented with an amplitude or frequency modulated signal, whereby neural oscillations are entrained to the modulation frequency. By modulating the input signal, for instance in a hearing aid, with a frequency within the alpha range, it is possible to facilitate listening by trigging the brain of the user to generate increased alpha activity.

By combining the findings regarding alpha activity with the ability to entrain neurons, the solutions aim at evoking more alpha activity through amplitude or frequency entrainment, in order to increase the individual's ability to inhibit irrelevant neural activity and thereby increase the listening performance. Preferably there is according to the present disclosure provided a wearable battery-driven device which can be use to process and present the auditory stimuli and possibly adapt the procedure to the individual. According to a specific embodiment, individual adaptation relies on physiological measures, especially EEG, measured from the device itself.

Measuring the alpha activity with an EEG sensor enables the listening device to predict when the wearer is ready to understand speech, and it can also delay speech in situations where audiovisual integration is not important (or delay audio and video in videoconference settings), such that the wearer is ready to understand speech.

The principles of the present disclosure can for instance be implemented by modulating the input signal as for example provided by a hearing aid microphone and suitably amplified or by adding an underlying auditory entraining signal when increased listening performance is required. Using EEG recordings made for instance by electrodes positioned in or at an ear of the user, an estimation of the cognitive load can be made and the modulation or the provision of the entrainment signal can be turned on/off accordingly. According to the present disclosure, it is also possible to use the EEG recordings to estimate the individual user's alpha peak frequency in order to individualize evoked alpha frequency. Further, according to the present disclosure, estimation of the alpha phase can be used to optimize the presentation of the entrainment signal. Each of these features, either separately or in combination, can lead to optimized speech understanding.

In the present specification the term "an auditory percept" is repeatedly used. This term is to be understood as a generic term comprising any auditory percept formed in a person, which may be the result of external auditory stimuli such as background noise or competing speech or be the result of internal sources, such as tinnitus.

According to the present disclosure there is further suggested a method and device for "attention optimized delay of speech". Human attention and focus varies continuously and a wearer of a listening device differs in readiness to understand speech. It would hence be advantageous to provide a method and/or a listening device, for instance a hearing aid, the can predict when the wearer is ready to understand a message.

Measuring the alpha activity in quiet periods, and comparing the power against an individual threshold the listening device can predict when the message should be played back. Another parameter is the maximal allowable delay which is individual and can also depend on the listening situation.

According to a specific implementation, the method, device and system of the present disclosure can be used to suppress tinnitus.

According to a practical implementation of the present disclosure there is provided a device, such as a hearing instrument, specifically a hearing aid, that presents a user with an amplitude or frequency modulated signal, whereby neural oscillations are entrained to the modulation frequency.

According to a practical implementation of the present disclosure there is provided a device, such as a hearing instrument, specifically a hearing aid, which device is able to detect difficult listening situation based on background SNR estimation applies an alpha modulation in the amplitude or frequency domain within the alpha range (approximately 6-13 Hz) to increase the production of inhibitory alpha activity.

According to a practical implementation of the present disclosure there is provided a device, such as a hearing instrument, specifically a hearing aid, that is able to measure the mental energy level of the wearer applies an alpha modulation in the amplitude or frequency domain within the alpha range (approximately 6-13 Hz) to increase the production of inhibitory alpha activity to cut back on mental resource spending in not so difficult situations.

According to a practical implementation of the present disclosure there is provided a device, such as a hearing instrument, specifically a hearing aid, that is provided with identifying means for identifying difficult listening situations, during which the alpha modulation technique should be applied, wherein the device or hearing aid is equipped with electrodes recording physiological data (EEG, EOG, ECG and skin resistance). Based on the physiological measures it is possible to identify situations during which the wearer has a high cognitive load and requires help to overcome the listening situation.

Within the alpha frequency range, subjects have their own individual alpha peak frequency, which is very consistent, although slightly decreasing with age. To ensure that the subject is able to utilize the entrainment alpha, it may be important to match this with the individual alpha peak frequency.

According to a practical implementation of the present disclosure there is provided a device, such as a hearing instrument, specifically a hearing aid, that is provided with monitoring means that monitor the listeners EEG, whereby it becomes possible to determine the individual alpha frequency within the range approximately 6-13 Hz and modulate the incoming signal to exactly that frequency.

According to a practical implementation of the present disclosure there is provided a device, such as a hearing instrument, specifically a hearing aid, wherein entrainment to amplitude or frequency modulated stimuli triggers a resetting of the alpha phase to that of the stimulation. This might induce an unwanted abruption in the neural alpha activity, which can affect the listening performance. By using EEG to monitor the listeners ongoing alpha oscillations, it is possible to phase lock the incoming modulated signals to that of the pre-existing alpha activity. It has been shown that listeners are better at detecting gaps in continuous sound stimuli if they are presented at the upward ramp of the alpha phase. This may have the result that presenting sound stimuli at an upward ramp could increase speech intelligibility.

The method and device according to the present disclosure can generally be used to inhibit irrelevant neural activity and thereby increase the listening performance. Such irrelevant, unwanted or disturbing neural activity (that leads to corresponding irrelevant, unwanted or disturbing auditory percepts in the users' brain) may for instance be background noises, for instance traffic or machinery noises, or competing speech, such as in a cocktail party environment. The unwanted auditory percept could, however, also be tinnitus, and the method and device according to the present disclosure may thus also be used for reducing the perception of tinnitus. It has thus been shown that tinnitus patients have lower alpha power, but can be trained to increase their alpha power with a consequent reduction of distress.

It is understood that although a listener's alpha activity is repeatedly mentioned in this specification, and is used in the various exemplifying implementations mentioned in the specification, it is also possible to base the principles of the method and device according to the present disclosure on neural activity in other frequency ranges. Specifically, beta activity (13-30 Hz), gamma activity (>30 Hz) and theta activity (4-7 Hz) could be used according to the teachings of the present disclosure.

According to a first aspect of the present disclosure there is provided a method for reducing a listener's task-irrelevant auditory perception using a hearing instrument or system, such as a hearing aid, comprising at least one input transducer configured to pick up the sound field in which the instrument or system is situated thereby providing an input signal, a signal processor configured to process the input signal, and an output transducer outputting the processed input signal, the method comprising the steps of:

providing in the hearing instrument or system a measuring device or system configured for measuring the listener's alpha, beta, gamma and/or theta activity;

providing in the hearing instrument or system a generation device or system configured for generating an alpha, beta, gamma and/or theta activity boosting signal that, when provided to the listener will increase the listener's ongoing alpha activity;

with said measuring device or system, establishing a first measure of the listener's alpha, beta, gamma and/or theta activity;

if the first measured alpha, beta, gamma and/or theta activity is below a predefined threshold, increasing the listener's ongoing alpha, beta, gamma and/or theta activity by the provision of said alpha, beta, gamma and/or theta activity boosting signal to the listener, and establishing a delayed version of said input signal, after a defined time interval establishing a second measure of the listener's alpha, beta, gamma and/or theta activity;

if by the second measure it is determined that the user's alpha, beta, gamma and/or theta activity is at or above a predefined threshold providing said delayed version of the input signal either with or without further processing to an output transducer in said device According to an alternative first aspect of the present disclosure there is provided a method for reducing a listener's task-irrelevant auditory perception, where the method comprises the steps of:

providing a measuring device or system configured for measuring the listener's alpha activity;

providing a generation device or system configured for generating an alpha activity boosting signal that, when provided to the listener will increase the listener's ongoing alpha activity;

with the measuring device or system, measure the listener's alpha activity;

if the measured alpha activity is below a predefined threshold, increasing the listener's ongoing alpha activity by the provision of the alpha activity boosting signal to the listener;

whereby the listener's ongoing alpha activity will be increased, resulting in facilitating reduction of task-irrelevant auditory perception, such as the auditory perception of noise or tinnitus, and thereby also increasing the listener's ability to understand speech under adverse listening conditions.

The method according to the first aspect or the alternative first aspect may include that after the defined time interval provided the user's alpha, beta, gamma and/or theta activity is below the predefined threshold, providing said alpha, beta, gamma and/or theta activity boosting signal to the listener and after a further instance of the defined time interval if the user's alpha, beta, gamma and/or theta activity is above the predefined threshold, providing the delayed version of the input signal, if after the further instance of the defined time interval the user's alpha, beta, gamma and/or theta activity is below the predefined threshold and the time since the first measurement does not exceed a maximum delay time threshold, repeating boost step and the delay step, if the time since the first measurement exceed a maximum delay time threshold providing the delayed version of the input signal to the user via the output transducer.

The defined time interval for repeating the measurement of the listener's alpha, beta, gamma and/or theta activity may be less than 100 milliseconds, such as less than 50 milliseconds, such as less than 25 milliseconds, such as less than 10 milliseconds, such as less than 5 milliseconds, such as less than 1 millisecond. Preferably the defined timer interval is chosen so that the alpha activity boosting signal may be provided at least once without causing so large a delay that the user perceives the delay as annoying and/or confusing.

According to an implementation of the first aspect and/or first alternative aspect of the present disclosure the method further comprising the steps of:

providing a listening device or system, such as a hearing instrument, comprising at least one input transducer configured to pick up the sound field in which the device or system is situated thereby providing an input signal;

based on the sound field picked up by said input transducer determining if a difficult listening situation exists;

if it is determined that a difficult listening situation exists, measuring the listener's alpha activity by the measuring device or system;

if it is determined that the listener's alpha activity is below a predefined threshold either boosting the listener's alpha activity by the provision to the listener of the alpha activity boosting signal, or providing a delayed version of said input signal;

repeating the measurement of the listener's alpha activity after a defined time interval;

if it is determined that the user's alpha activity is at or above a predefined threshold providing the input signal or said delayed version hereof either with or without further processing to an output transducer in said device, the output of which transducer is picked up by an ear of the listener.

According to an implementation of the first aspect and/or first alternative aspect of the present disclosure the determination that a difficult listening situation exists is based on measured signal-to-noise (SNR) ratio of said input signal.

According to an implementation of the first aspect and/or first alternative aspect of the present disclosure the listener's alpha activity is determined based on measured EEG.

According to an implementation of the first aspect and/or first alternative aspect of the present disclosure the boost of alpha activity is obtained through neural entrainment.

According to an implementation of the first aspect and/or first alternative aspect of the present disclosure the peak frequency of the alpha activity boosting signal corresponds to the individual listener's alpha activity.

According to an implementation of the first aspect and/or first alternative aspect of the present disclosure the listener's alpha activity (or cognitive load) is determined based on measurements of any of the group of parameters comprising EOG, ECG and skin resistance.

According to a second aspect of the present disclosure there is provided a listening device, such as a hearing instrument, and still more specifically a hearing aid, for reducing a listener's task-irrelevant auditory perception, comprising:

an indicator for indicating to the device that a situation comprising task-irrelevant auditory perception is present;

an input transducer configured to pick up the sound field in which the device is situated thereby providing an input signal for further processing in the device;

a measuring device or system configured for measuring the listener's alpha activity;

a generation device or system configured for generating an alpha activity boosting signal that, when provided to the listener will increase the listener's ongoing alpha activity;

a boosting signal providing device or system configured for providing the listener with said alpha activity boosting signal;

a processor for processing said input signal and providing the processed signal to the listener through an output transducer.

According to an implementation of the second aspect of the present disclosure the listening device the indicator is a signal-to-noise ratio (SNR) estimator configured to estimate SRN between a wanted signal and a background noise signal thereby providing a SRN signal corresponding to the estimated SNR.

According to an implementation of the second aspect of the present disclosure the listening device the measuring device or system configured for measuring the listener's alpha activity comprises an EEG sensor.

According to an implementation of the second aspect of the present disclosure the listening device the measuring device or system configured for measuring the listener's alpha activity comprises one or more sensors belonging to the group comprising EOG, EEG or ECG sensors and skin resistance sensors.

According to an implementation of the second aspect of the present disclosure the listening device the boost of alpha activity is obtained through neural entrainment.

According to an implementation of the second aspect of the present disclosure the listening device the peak frequency of the alpha activity boosting signal corresponds to the individual listener's alpha activity.

According to an implementation of the second aspect of the present disclosure the listening device comprises: an alpha activity level decision unit and an adjustable delay; wherein the alpha activity decision unit is configured such that when the listener's measured alpha activity is below a predefined threshold, the alpha activity decision unit provides a delay control signal to the adjustable delay, whereby the input signal provided by the input transducer is delayed a period of time.

According to a third aspect of the present disclosure there is provided a signal processing system configured to execute the method described above.

BRIEF DESCRIPTION OF DRAWINGS

The aspects of the disclosure may be best understood from the following detailed description taken in conjunction with the accompanying figures. The figures are schematic and simplified for clarity, and they merely show details to improve the understanding of the claims, while other details are left out. Throughout, the same reference numerals are used for identical or corresponding parts. The individual features of each aspect may each be combined with any or all features of the other aspects. These and other aspects, features and/or technical effects will be apparent from and elucidated with reference to the illustrations described hereinafter in which:

FIG. 6 shows a flow chart illustrating an implementation of the method of utilizing a signal delay based on measured alpha activity in order to improve speech perception according to the present disclosure.

DETAILED DESCRIPTION

Figure 1:
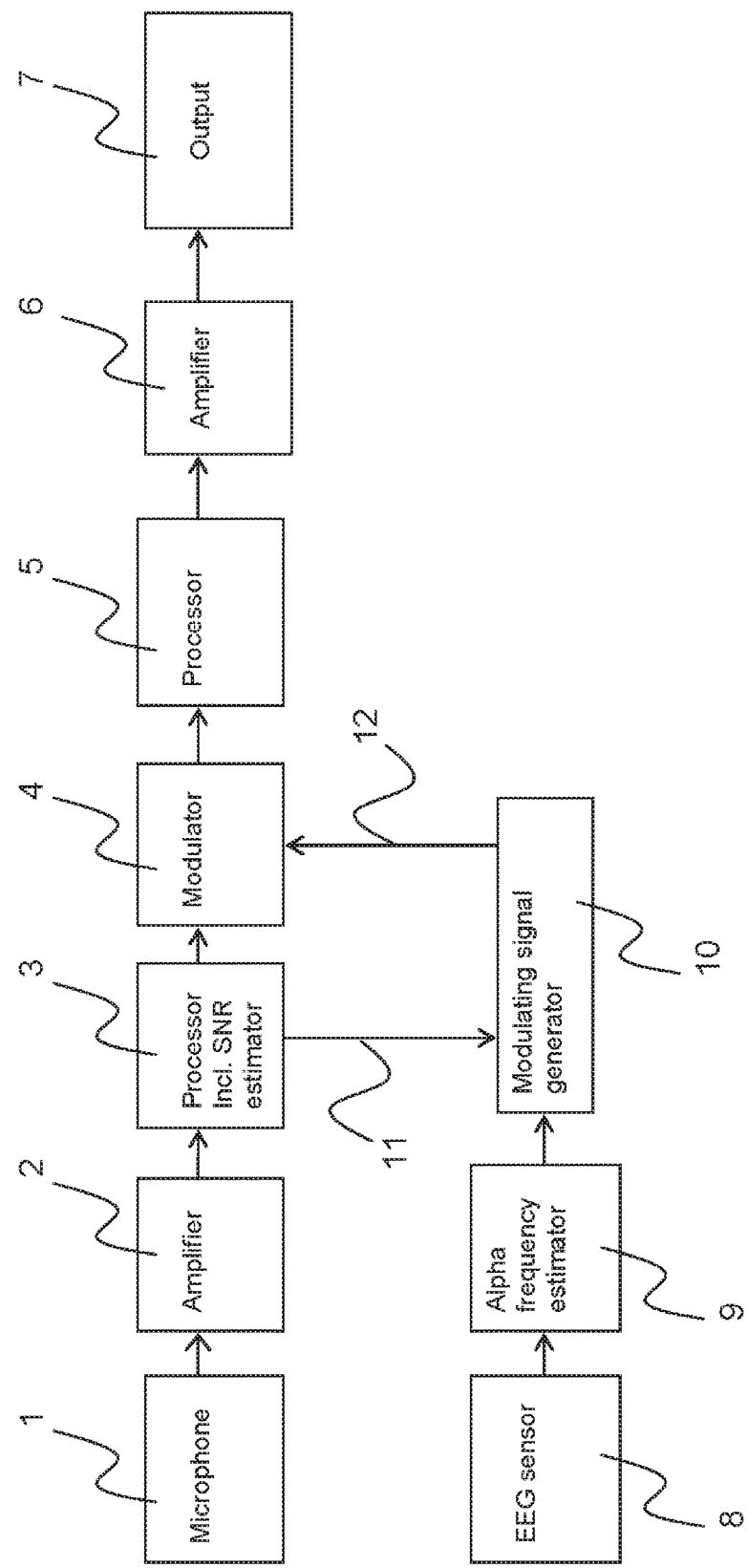
FIG. 1 shows a schematic block diagram illustrating a hearing aid comprising means for boosting alpha activity of a user according to a practical implementation of the present disclosure.

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include microprocessors, microcontrollers, digital signal processors (DSPs), field programmable gate arrays (FPGAs), programmable logic devices (PLDs), gated logic, discrete hardware circuits, and other suitable hardware configured to perform the various functionality described throughout this disclosure. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

A hearing device may include a hearing aid that is adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. The "hearing device" may further refer to a device such as an earphone or a headset adapted to receive an audio signal electronically, possibly modifying the audio signal and providing the possibly modified audio signals as an audible signal to at least one of the user's ears. Such audible signals may be provided in the form of an acoustic signal radiated into the user's outer ear, or an acoustic signal transferred as mechanical vibrations to the user's inner ears through bone structure of the user's head and/or through parts of middle ear of the user or electric signals transferred directly or indirectly to cochlear nerve and/or to auditory cortex of the user.

The hearing device is adapted to be worn in any known way. This may include i) arranging a unit of the hearing device behind the ear with a tube leading air-borne acoustic signals into the ear canal or with a receiver/loudspeaker arranged close to or in the ear canal such as in a Behind-the-Ear type hearing aid, and/or ii) arranging the hearing device entirely or partly in the pinna and/or in the ear canal of the user such as in a In-the-Ear type hearing aid or In-the-Canal/Completely-in-Canal type hearing aid, or iii) arranging a unit of the hearing device attached to a fixture implanted into the skull bone such as in Bone Anchored Hearing Aid or Cochlear Implant, or iv) arranging a unit of the hearing device as an entirely or partly implanted unit such as in Bone Anchored Hearing Aid or Cochlear Implant.

A "hearing system" refers to a system comprising one or two hearing devices, and a "binaural hearing system" refers to a system comprising two hearing devices where the devices are adapted to cooperatively provide audible signals to both of the user's ears. The hearing system or binaural hearing system may further include auxiliary device(s) that communicates with at least one hearing device, the auxiliary device affecting the operation of the hearing devices and/or benefiting from the functioning of the hearing devices. A wired or wireless communication link between the at least one hearing device and the auxiliary device is established that allows for exchanging information (e.g. control and status signals, possibly audio signals) between the at least one hearing device and the auxiliary device. Such auxiliary devices may include at least one of remote controls, remote microphones, audio gateway devices, mobile phones, public-address systems, car audio systems or music players or a combination thereof. The audio gateway is adapted to receive a multitude of audio signals such as from an entertainment device like a TV or a music player, a telephone apparatus like a mobile telephone or a computer, a PC. The audio gateway is further adapted to select and/or combine an appropriate one of the received audio signals (or combination of signals) for transmission to the at least one hearing device. The remote control is adapted to control functionality and operation of the at least one hearing devices. The function of the remote control may be implemented in a SmartPhone or other electronic device, the SmartPhone/electronic device possibly running an application that controls functionality of the at least one hearing device.

In general, a hearing device includes i) an input unit such as a microphone for receiving an acoustic signal from a user's surroundings and providing a corresponding input audio signal, and/or ii) a receiving unit for electronically receiving an input audio signal. The hearing device further includes a signal processing unit for processing the input audio signal and an output unit for providing an audible signal to the user in dependence on the processed audio signal.

The input unit may include multiple input microphones, e.g. for providing direction-dependent audio signal processing. Such directional microphone system is adapted to enhance a target acoustic source among a multitude of acoustic sources in the user's environment. In one aspect, the directional system is adapted to detect (such as adaptively detect) from which direction a particular part of the microphone signal originates. This may be achieved by using conventionally known methods. The signal processing unit may include amplifier that is adapted to apply a frequency dependent gain to the input audio signal. The signal processing unit may further be adapted to provide other relevant functionality such as compression, noise reduction, etc. The output unit may include an output transducer such as a loudspeaker/receiver for providing an air-borne acoustic signal transcutaneously or percutaneously to the skull bone or a vibrator for providing a structure-borne or liquid-borne acoustic signal. In some hearing devices, the output unit may include one or more output electrodes for providing the electric signals such as in a Cochlear Implant.

The principles of the present disclosure can for instance be implemented by modulating the input signal as for example provided by a hearing aid microphone and suitably amplified or by adding an underlying auditory entraining signal when increased listening performance is required. Using EEG recordings made for instance by electrodes positioned in or around an ear of the user, an estimation of the cognitive load can be made and the modulation or the provision of the entrainment signal can be turned on/off accordingly. According to the present disclosure, it is also possible to use the EEG recordings to estimate the individual user's alpha peak frequency in order to individualize evoked alpha frequency. Further, according to the present disclosure, estimation of the alpha phase can be used to optimize the presentation of the entrainment signal. Each of these features, either separately or in combination, can lead to optimized speech understanding.

It is possible to implement the teachings of the present disclosure in many ways, as for instance as follows, but it is understood that these and other examples of practical implementations described in the detailed description of the disclosure and in the drawings are to be regarded as non-limiting examples.

A possible practical implementation of the teachings of the present disclosure is a hearing aid that is provided with detection means that are able to detect difficult listening situation based on background SNR estimation and which applies an alpha modulation in the amplitude or frequency domain within the alpha range (approximately 6-13 Hz, such as around 10 Hz) to increase the production of inhibitory alpha activity.

A possible practical implementation of the teachings of the present disclosure is a hearing aid that is provided with measuring means that are able to measure the mental energy level of the wearer and which applies an alpha modulation in the amplitude or frequency domain within the alpha range (approximately 6-13 Hz, such as around 10 Hz) to increase the production of inhibitory alpha activity to cut back on mental resource spending in not so difficult situations.

A possible practical implementation of the teachings of the present disclosure is a hearing aid that is provided with identification means that can identify difficult listening situations during which the alpha modulation technique should be applied, using a hearing aid device equipped with electrodes recording physiological data, such as EEG, EOG, ECG and skin resistance. Based on the physiological measures it is possible to identify situations during which the wearer has a high cognitive load and requires help to overcome the listening situation.

A possible practical implementation of the teachings of the present disclosure is a hearing aid that is provided with monitoring means that are configured to determine the individual user's alpha peak frequency. Within the alpha frequency range, subjects has their own individual alpha peak frequency, which is very consistent, although slightly decreasing with age. To ensure that the subject is able to utilize the entrainment alpha, it is important to match this with the individual alpha peak frequency. By monitoring the listeners EEG, it is possible to determine the individual alpha frequency within the range approximately 6-13 Hz, such as around 10 Hz, and modulate the incoming signal to exactly that frequency.

A possible practical implementation of the teachings of the present disclosure is a hearing aid in which entrainment to amplitude or frequency modulated stimuli triggers a resetting of the alpha phase to that of the stimulation, thereby preventing an unwanted abruption in the neural alpha activity, which can affect the listening performance. By using EEG to monitor the listeners ongoing alpha oscillations, it is possible to phase lock the incoming modulated signals to that of the pre-existing alpha activity.

Figure 2:
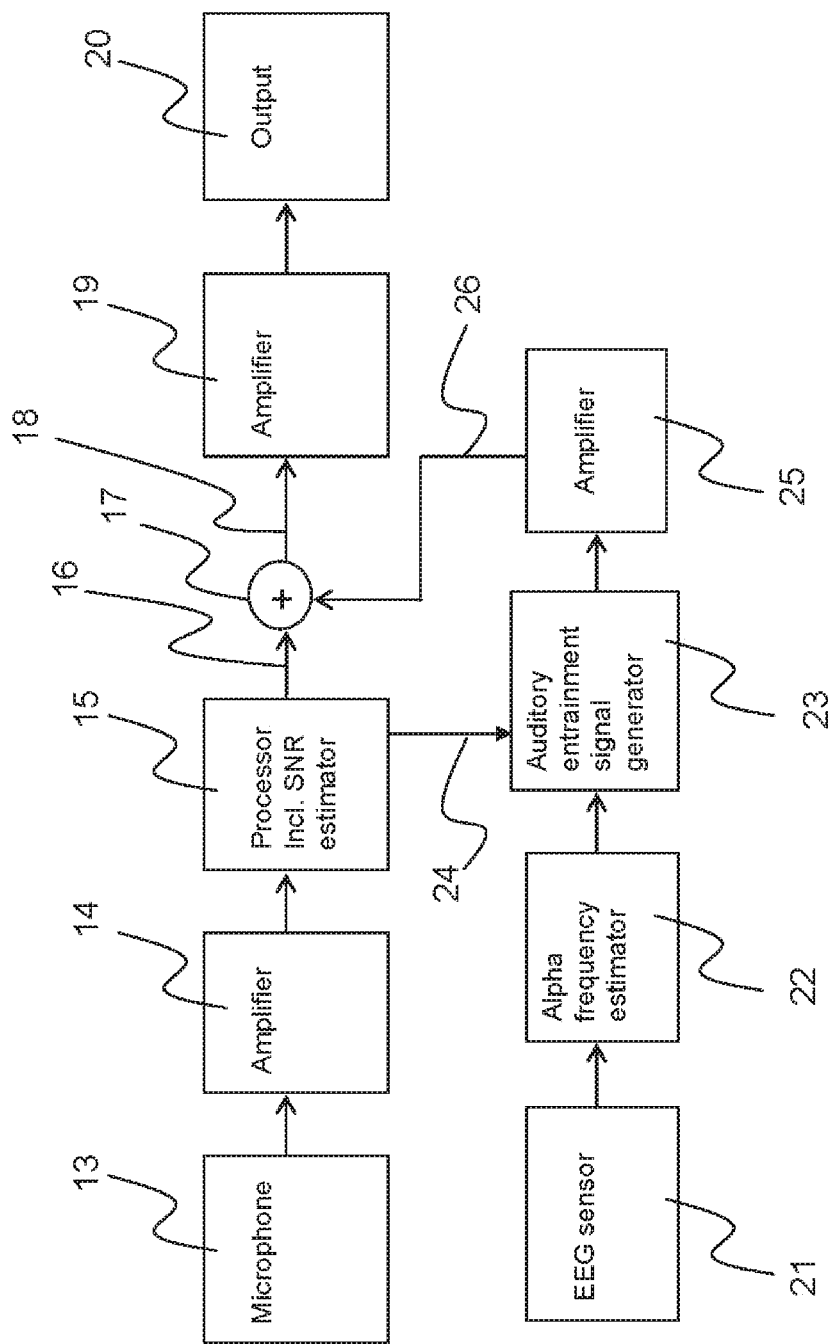
FIG. 2 shows a schematic block diagram illustrating a hearing aid comprising alternative means for boosting alpha activity of a user according to another practical implementation of the present disclosure.
Figure 3:
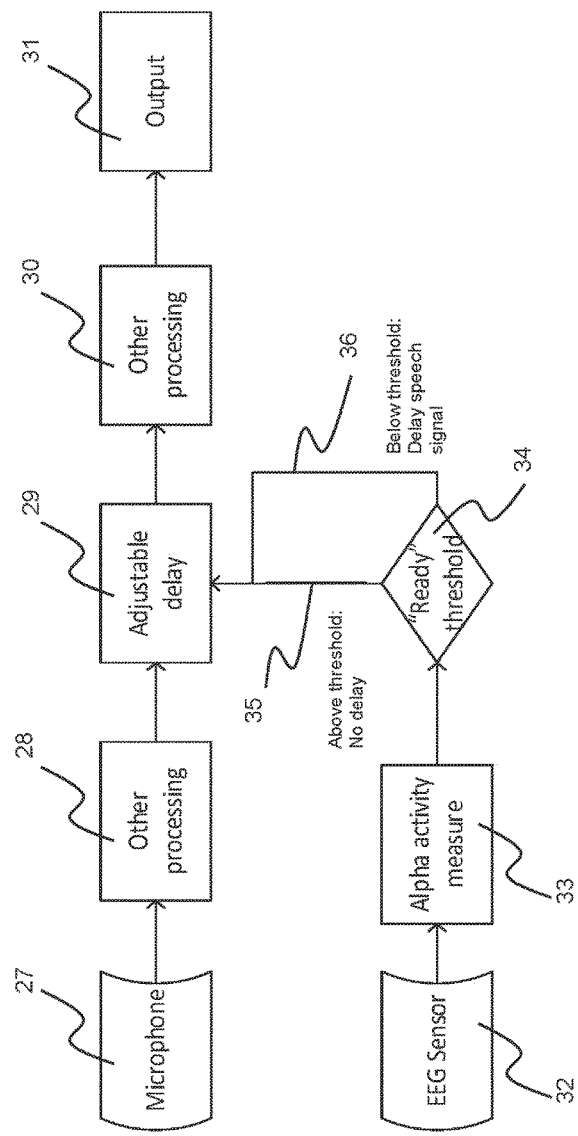
FIG. 3 shows a schematic block diagram illustrating a hearing aid comprising means for attention optimized delay of speech according to still another practical implementation of the present disclosure.
Figures 4, 5:
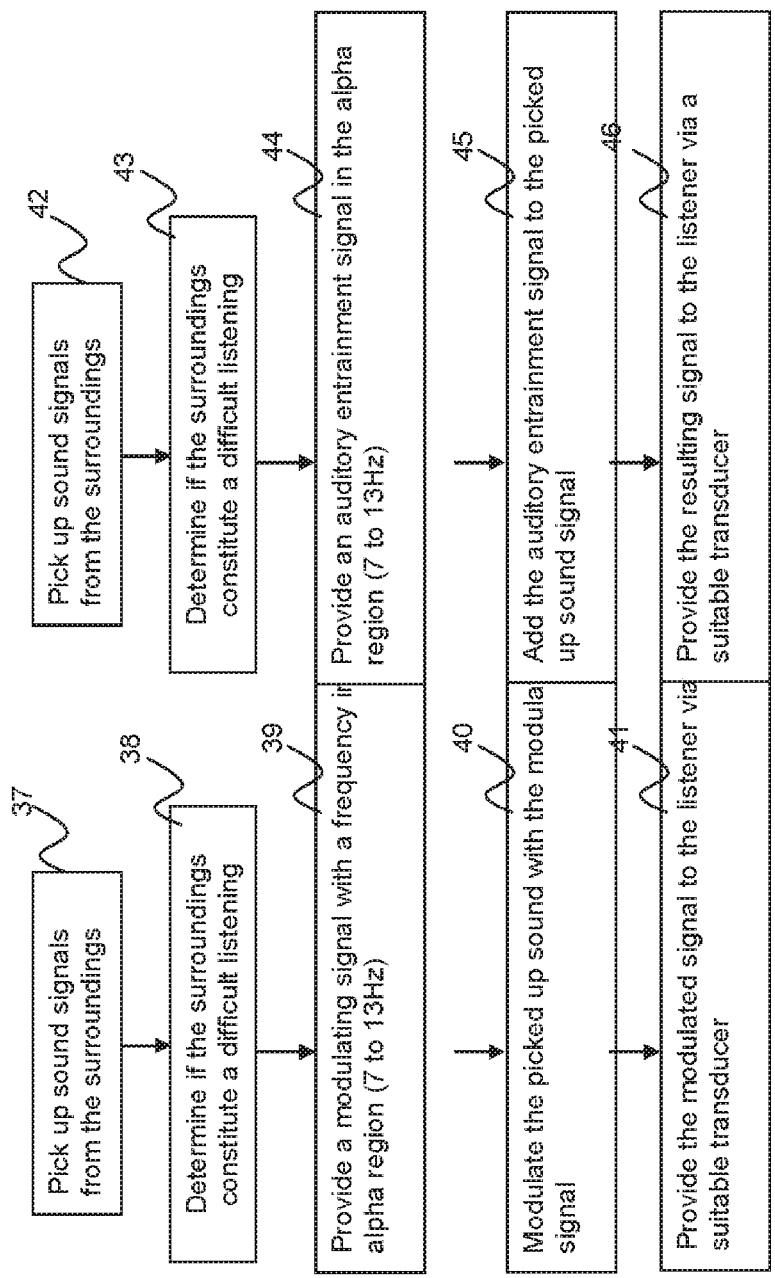
FIG. 4 shows a flow chart illustrating a first implementation of the method of utilizing a boost of alpha activity to improve speech perception according to the present disclosure.
FIG. 5 shows a flow chart illustrating a second implementation of the method of utilizing a boost of alpha activity to improve speech perception according to the present disclosure.

Some practical implementations of the teachings of the present disclosure are illustrated in FIGS. 1, 2 and 3 and the corresponding methods are illustrated by the flow charts shown in FIGS. 4, 5 and 6.

Now referring to FIG. 1 there is shown a schematic block diagram of a practical implementation of the present disclosure comprising a hearing aid provided with means for boosting alpha activity of a user. The hearing aid comprises an input transducer, such as a microphone, 1, the output signal of which is provided to input terminals of an amplifier 2 in order to amplify the signal from the input transducer sufficiently for the further processing in the hearing aid. The amplified output signal from amplifier 2 is provided to a processor 3 that includes a signal to noise ratio (SNR) estimator, but which processor may additionally comprise other functions needed in a hearing aid. The output signal from the processor 3 is provided to a modulator 4, the output signal of which is provided to a processor 5 that is configured for carrying out different functions of the hearing aid, such as frequency-dependent gain and compression. The processed output signal from processor 5 is provided to an output amplifier 6 that provides the necessary signal to the output transducer 7, such as a receiver.

The hearing aid shown in FIG. 1 further comprises one or more EEG sensors 8 that can monitor the EEG of the user of the hearing aid. Based on the output signal from the EEG sensor, the alpha frequency estimator 9 estimates the individual alpha frequency of the user. Information of the individual alpha frequency is provided to a modulating signal generator 10 that provides a modulating frequency that is optimally adapted to the particular user to the modulator 4.

The processor 3 provides, in addition to the processed output signal for the modulator 4, a SNR estimation signal on line 11 that is used to activate the modulating signal generator 10. This activation takes place when the SNR is judged so low that the listening situation becomes problematic, and hence that alpha activity boost is needed.

The amplified input signal from the input transducer 1 is hence modulated by the user's individual alpha frequency whenever the listening situation indicates that a boost of alpha activity is needed. In this manner, optimal alpha activity boost for the individual user can be obtained.

With reference to FIG. 2 there is shown a schematic block diagram illustrating a hearing aid comprising alternative means for boosting alpha activity of a user according to another practical implementation of the present disclosure. The hearing aid comprises an input transducer, such as a microphone 13, the output signal of which is amplified sufficiently by an amplifier 14 to be provided to the processor 15 that may provide various functions necessary for treatment of the hearing impairment. As in the implementation shown in FIG. 1, the processor 15 also includes a signal-to-noise ratio (SNR) estimator that can provide a SNR estimation signal on line 24. The processed output signal 16 from the processor 15 is provided to an adder 17, the output signal 18 of which is amplified in an amplifier 19 before being provided to an output transducer, such as a receiver 20.

The hearing aid shown in FIG. 2 further comprises an EEG sensor 21 that can monitor the EEG of the user of the hearing aid. Based on the output signal from the EEG sensor, the alpha frequency estimator 22 estimates the individual alpha frequency of the user. The estimated alpha frequency is used to control an auditory entrainment signal generator 23 that generates an auditory entrainment signal, which is being amplified sufficiently by an amplifier 25 such that the amplified auditory entrainment signal 26 can be added to the amplified and processed input signal from the input transducer 13. This is done in the adder 17.

Also in this implementation, boost of alpha activity is governed by the individual users own peak alpha frequency, thereby optimizing individual alpha boost, and the alpha activity boost takes place when the listening situation requires it, controlled by the SNR estimation signal 24 provided by the processor 15, which signal activates the auditory entrainment signal generator 23.

Now referring to FIG. 3, there is shown a hearing aid according to an alternative, practical implementation of the present disclosure, in which improved speech perception is not obtained by boosting the individual user's alpha activity. Instead, in this implementation, the user's alpha activity is monitored ongoing by the EEG sensor 32 and the output signal from the EEG sensor is used to derive a measure of the ongoing alpha activity. This measure is derived in the alpha activity measure unit 33. It has surprisingly been discovered that there is a connection between alpha activity that occurs just before the presentation of speech to a listener and the listener's speech recognition score. I.e. the higher the alpha activity just before reception of speech, the better will be the speech recognition (although alpha activity cannot increase infinitely, but is subject to an alpha power ceiling).

In the implementation of a hearing aid according to the present disclosure shown in FIG. 3, the measured alpha activity provided by the alpha activity measure unit 33 is compared with a chosen threshold that indicates, whether the user is considered ready to understand speech or not. This comparison takes place in a "ready" threshold functional block 34, which in a practical implementation may be implemented by a comparator. If it is judged that the measured alpha activity is sufficiently high, i.e. above the "ready" threshold, the user is ready to understand speech sufficiently well and the processed signal from the input transducer, such as a microphone 27, suitably processed in a signal processor 28 is passed through the adjustable delay unit 29 without delay and on the a pre-processing stage 30 from which it is provided to the output transducer 31, such as a hearing aid receiver. If, on the contrary, it is judged that the measured alpha activity is too low, i.e. below the "ready" threshold, the processed signal from the processor 28 is delayed in the adjustable delay unit 29, until the measured alpha activity is judged sufficiently high to ensure acceptable speech recognition.

It is possible according to a specific implementation of the present disclosure to combine the alpha activity boost implementations as for instance illustrated in FIG. 1 or 2 with the signal delay implementation illustrated in FIG. 3. This can be done in alternative ways. As a first possible implementation, it is judged by a system corresponding to that of FIG. 3 whether the measured alpha activity is sufficiently high to ensure acceptable speech recognition. If this is not the case, i.e. the measured alpha activity is below the "ready" threshold, the processed input signal is delayed as described above, but if alpha activity still remains low after a certain period of time it is attempted to boost alpha activity by neural entrainment, as illustrated in FIG. 1 or 2. As a second alternative, a too low measured alpha activity is initially boosted and if the resulting boosted alpha activity is still below the "ready" threshold, the processed signal is delayed, until a sufficiently high alpha activity is measured.

It is understood that the above three specific implementations of a device according to the present disclosure are only meant as examples of circuit configurations that may implement the concepts of the present disclosure and that other circuit configurations may be conceived by a skilled person without departing from the scope of protection of the present specification.

Below, the operational methods implemented by the devices shown in FIGS. 1, 2 and 3 are summarized by means of respective flow charts.

Referring to FIG. 4 there is shown a flow chart illustrating a first implementation of the method of utilizing a boost of alpha activity to improve speech perception according to the present disclosure. In functional block 37 sounds from the surroundings are picked up for instance by a hearing aid microphone. In block 38 it is determined if the surroundings constitute a difficult listening situation. This determination can for instance ne based on measured or estimated signal-to-noise ratio. If it is determined that the listening situation is difficult, a modulating signal with a frequency in the alpha region (approximately 7 to 13 Hz) is provided in block 39 and the picked up sound signal from the surroundings are modulated by this modulating signal in block 40. In block 41 the modulated signal, i.e. the signal picked up from the surroundings modulated by the modulating signal is provided to the listener for instance through a hearing aid receiver.

Referring to FIG. 5 there is shown a flow chart illustrating a second implementation of the method of utilizing a boost of alpha activity to improve speech perception according to the present disclosure. The functional blocks 42 and 43, respectively, correspond to blocks 37 and 38 in FIG. 4. In block 44 there is provided an auditory entrainment signal with a frequency in the alpha region and this signal is in block 45 added to the signal picked up from the surroundings. The resulting signal is finally provided to the listener in block 46 for instance through a hearing aid receiver.

Referring to FIG. 6 the is shown a flow chart illustrating an implementation of the method of utilizing a signal delay based on measured alpha activity in order to improve speech perception according to the present disclosure. The sound signals from the surroundings are picked up by an input transducer 47 and the listeners ongoing alpha activity is measured in block 48 for instance by means of an EEG measurement sensor. In block 49 it is evaluated whether the measured alpha activity is below or above a predefined threshold (the "ready" threshold). If the alpha activity is below the threshold, the input signal is delayed in block 51 and the delayed version passed on (ref. number 52) to the listener via a suitable output transducer in block 53. If the measured alpha activity is judged to be above the threshold, the input signal is passed on to the output transducer without delay (ref. number 50).

In an aspect of the present disclosure, the various functions described above may be stored on or encoded as instructions or code on a tangible computer-readable medium. The computer readable medium includes computer storage media adapted to store a computer program comprising program codes, which when run on a processing system causes the data processing system to perform at least some (such as a majority or all) of the steps of the method described above.

By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media. In addition to being stored on a tangible medium, the computer program can also be transmitted via a transmission medium such as a wired or wireless link or a network, e.g. the Internet, and loaded into a data processing system for being executed at a location different from that of the tangible medium.

In an aspect, the present disclosure relates to a data processing system comprising a processor adapted to execute the computer program for causing the processor to perform at least some (such as a majority or all) of the steps of the method described above and in the claims.

It is intended that the structural features of the devices described above, either in the detailed description and/or in the claims, may be combined with steps of the method, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening elements may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. A method for reducing a listener's task-irrelevant auditory perception using a hearing instrument or system, such as a hearing aid, comprising at least one input transducer configured to pick up the sound field in which the instrument or system is situated thereby providing an input signal, a signal processor configured to process the input signal, and an output transducer outputting the processed input signal, the method comprising the steps of:

providing in the hearing instrument or system a measuring device or system configured for measuring the listener's alpha, beta, gamma and/or theta activity;

providing in the hearing instrument or system a generation device or system configured for generating an alpha, beta, gamma and/or theta activity boosting signal that, when provided to the listener will increase the listener's ongoing alpha activity;

with said measuring device or system, establishing a first measure of the listener's alpha, beta, gamma and/or theta activity;

if the first measured alpha, beta, gamma and/or theta activity is below a predefined threshold, increasing the listener's ongoing alpha, beta, gamma and/or theta activity by the provision of said alpha, beta, gamma and/or theta activity boosting signal to the listener, and establishing a delayed version of said input signal, after a defined time interval establishing a second measure of the listener's alpha, beta, gamma and/or theta activity;

if by the second measure it is determined that the user's alpha, beta, gamma and/or theta activity is at or above a predefined threshold providing said delayed version of the input signal either with or without further processing to an output transducer in said device.

2. The method according to claim 1, wherein after the defined time interval provided the user's alpha, beta, gamma and/or theta activity is below the predefined threshold, providing said alpha, beta, gamma and/or theta activity boosting signal to the listener and after a further instance of the defined time interval if the user's alpha, beta, gamma and/or theta activity is above the predefined threshold, providing the delayed version of the input signal, if after the further instance of the defined time interval the user's alpha, beta, gamma and/or theta activity is below the predefined threshold and the time since the first measurement does not exceed a maximum delay time threshold, repeating boost step and the delay step, if the time since the first measurement exceed a maximum delay time threshold providing the delayed version of the input signal to the user via the output transducer.

3. The method according to claim 1, wherein the defined time interval for repeating the measurement of the listener's alpha, beta, gamma and/or theta activity is less than 100 milliseconds, such as less than 50 milliseconds, such as less than 25 milliseconds, such as less than 10 milliseconds, such as less than 5 milliseconds, such as less than 1 millisecond.

4. The method according to claim 1, wherein the determination that a difficult listening situation exists is based on measured signal-to-noise (SNR) ratio of said input signal.

5. The method according to claim 1, wherein the listener's alpha, beta, gamma and/or theta activity is determined based on measured EEG, optionally, wherein the listener's alpha, beta, gamma and/or theta activity is determined based on measurements of any of the group of parameters comprising EOG, ECG and skin resistance.

6. The method according to claim 1, wherein said boost of alpha, beta, gamma and/or theta activity is obtained through neural entrainment.

7. The method according to claim 1, wherein the peak frequency of the alpha, beta, gamma and/or theta activity boosting signal corresponds to the individual listener's alpha, beta, gamma and/or theta activity.

8. A hearing instrument, such as a hearing aid, configured for reducing a user's task-irrelevant auditory perception, comprising:

an indicator for indicating to the hearing instrument that a situation comprising task-irrelevant auditory perception is present;

an input transducer configured to pick up the sound field in which the hearing instrument is situated thereby providing an input signal for further processing in the hearing instrument;

a measuring device or system configured for measuring the user's alpha, beta, gamma and/or theta activity;

a generation device or system configured for generating an alpha, beta, gamma and/or theta activity boosting signal that, when provided to the user will increase the user's ongoing alpha, beta, gamma and/or theta activity;

a boosting signal providing device or system configured for providing the user with said alpha, beta, gamma and/or theta activity boosting signal;

a processor for processing said input signal and providing the processed signal to the user through an output transducer, an alpha, beta, gamma and/or theta activity level decision unit;

an adjustable delay;

wherein the alpha, beta, gamma and/or theta activity decision unit is configured such that when the user's measured alpha, beta, gamma and/or theta activity is below a predefined threshold, the alpha, beta, gamma and/or theta activity decision unit provides a delay control signal to the adjustable delay, whereby the input signal provided by the input transducer is delayed a period of time.

9. The hearing instrument according to claim 8, in which said indicator is a signal-to-noise ratio (SNR) estimator configured to estimate SRN between a wanted signal and a background noise signal thereby providing a SRN signal corresponding to the estimated SNR.

10. The hearing instrument according to claim 8, in which said measuring device or system configured for measuring the user's alpha, beta, gamma and/or theta activity comprises an EEG sensor.

11. The hearing instrument according to claim 8, in which said measuring device or system configured for measuring the user's alpha, beta, gamma and/or theta activity comprises one or more sensors belonging to the group comprising EOG sensors, ECG sensors and skin resistance sensors.

12. The hearing instrument according to claim 8, wherein said boost of alpha, beta, gamma and/or theta activity is obtained through neural entrainment.

13. The hearing instrument according to claim 1, wherein the peak frequency of the alpha, beta, gamma and/or theta activity boosting signal corresponds to the individual user's alpha, beta, gamma and/or theta activity.

14. A signal processing system configured to execute the method according to claim 1.

15. The method according to claim 2, wherein the defined time interval for repeating the measurement of the listener's alpha, beta, gamma and/or theta activity is less than 100 milliseconds, such as less than 50 milliseconds, such as less than 25 milliseconds, such as less than 10 milliseconds, such as less than 5 milliseconds, such as less than 1 millisecond.

16. The method according to claim 2, wherein the determination that a difficult listening situation exists is based on measured signal-to-noise (SNR) ratio of said input signal.

17. The method according to claim 3, wherein the determination that a difficult listening situation exists is based on measured signal-to-noise (SNR) ratio of said input signal.

18. The method according to claim 2, wherein the listener's alpha, beta, gamma and/or theta activity is determined based on measured EEG, optionally, wherein the listener's alpha, beta, gamma and/or theta activity is determined based on measurements of any of the group of parameters comprising EOG, ECG and skin resistance.

19. The method according to claim 3, wherein the listener's alpha, beta, gamma and/or theta activity is determined based on measured EEG, optionally, wherein the listener's alpha, beta, gamma and/or theta activity is determined based on measurements of any of the group of parameters comprising EOG, ECG and skin resistance.

20. The method according to claim 4, wherein the listener's alpha, beta, gamma and/or theta activity is determined based on measured EEG, optionally, wherein the listener's alpha, beta, gamma and/or theta activity is determined based on measurements of any of the group of parameters comprising EOG, ECG and skin resistance.

\* \* \* \* \*